United States Patent [19]

Yako et al.

[11] Patent Number: 5,455,364

[45] Date of Patent: Oct. 3, 1995

[54] PROCESS FOR REMOVING AN IMPURITY IN ORGANOMETALLIC COMPOUND

[75] Inventors: Tadaaki Yako; Yasuo Oga, both of Ehime, Japan

[73] Assignee: Sumitomo Chemical Company, Ltd., Osaka, Japan

[21] Appl. No.: 357,171

[22] Filed: Dec. 13, 1994

[30] Foreign Application Priority Data

Dec. 14, 1993 [JP] Japan ................................ 5-313388

[51] Int. Cl.$^6$ ........................................... C07F 5/00
[52] U.S. Cl. ................................... 556/1; 556/27
[58] Field of Search ............................ 556/1, 27

[56] References Cited

U.S. PATENT DOCUMENTS

| | | | |
|---|---|---|---|
| 4,797,500 | 1/1989 | Kadokura et al. | 556/1 |
| 4,847,399 | 7/1989 | Hallock et al. | 556/1 |
| 5,084,128 | 1/1992 | Baker | 156/614 |
| 5,288,885 | 2/1994 | Smit et al. | 556/1 |
| 5,350,869 | 9/1994 | Kanjolia et al. | 556/1 |

FOREIGN PATENT DOCUMENTS

| | | |
|---|---|---|
| 0523525 | 1/1993 | European Pat. Off. . |
| 4005726 | 10/1990 | Germany . |
| 1100178 | 4/1989 | Japan . |
| 2-67230 | 3/1990 | Japan . |
| 3-112991 | 5/1991 | Japan . |
| 2123423 | 2/1984 | United Kingdom . |
| 2183651 | 6/1987 | United Kingdom . |

OTHER PUBLICATIONS

Chemical Abstract 113:24230c (1990).

*Primary Examiner*—Porfirio Nazario-Gonzalez
*Attorney, Agent, or Firm*—Birch, Stewart, Kolasch & Birch

[57] ABSTRACT

The present invention provides a process for removing an oxygen-containing component in a crude organometallic compound consisting essentially of an organometallic compound of the general formula (1):

$$R_1R_2MX \qquad (1)$$

wherein $R_1$ and $R_2$ independently represent an alkyl group or a cycloalkadienyl group, M represents a Ga atom or an In atom and X represents an alkyl group, a halogen atom or a hydrogen atom, and the oxygen-containing component as an impurity, which comprises the steps of mixing the crude organometallic compound and an alkali halide in an amount of 0.1 to 10% by weight of the crude organometallic compound, heat-treating the mixture, and vaporizing the organometallic compound for separation, the steps being carried out in a substantially oxygen-free atmosphere.

10 Claims, No Drawings

PROCESS FOR REMOVING AN IMPURITY IN ORGANOMETALLIC COMPOUND

BACKGROUND OF THE INVENTION

1. Field of the Invention

The present invention relates to a process for purifying an organometallic compound. More particularly, it relates to a process for removing a trace amount of oxygen-containing component contained in an organometallic compound which is used as a raw material in the field of compound semiconductors.

2. Description of the Related Art

Organometallic compounds are recently used as raw materials for forming a thin film of a compound semiconductor by metal organic chemical vapor deposition (referred to as "MOCVD" hereinafter).

The thin film is not only utilized as a light-emitting diode, a laser diode and a microwave element but also is starting to be utilized as an ultraspeed IC and a opto-electronic IC.

However, the organometallic compound contains an oxygen-containing component as an impurity, which is formed by the reaction of the organometallic compound with air or moisture inevitably mixed during preparation or handling processes of the organometallic compound.

When the organometallic compound containing such the oxygen-containing component as an impurity is subjected to the above MOCVD, oxygen atoms are incorporated in the thin layer of the semiconductor. As the result, its electric and optical characteristics are extremely deteriorated to cause problems, for example, that only a film having high resistivity or low luminescent efficiency is obtained, or that elements using the thin layer have a short life even if a film having satisfactory properties could be obtained.

A fractional distillation method usually adopted for removing an impurity, i.e. the oxygen-containing component, cannot reduce its content in the organometallic compound to below hundreds of ppm since the vapor pressure of the oxygen-containing component is similar to that of the organometallic compound.

Japanese Patent Kokai No. 67230/1990 proposes a process for purifying an organometallic compound containing an oxygen-containing component in which it is treated with a hydrogenated metal compound such as sodium hydride, lithium aluminum hydride, etc. in an amount of 0.1 to 50% by weight, based on the organometallic compound.

Japanese Patent Kokai No. 112991/1991 proposes a process for purifying an alkyl aluminum containing an oxygen-containing component in which it is treated with an aluminum halide such as aluminum bromide, aluminum iodide, etc.

However, since the hydrogenated metal compound or the aluminum halide mentioned above itself has high decomposition tendency by moisture, these processes have problems, for example, that their dealing should be strictly controlled for maintenance or control of the activities of the reagents, and that reproducibility of the effect is poor. Therefore, a process for purifying organometallic compounds which does not have such the problems and is industrially excellent is desired.

SUMMARY OF THE INVENTION

It is an object of the present invention to provide a process for purifying an organometallic compound in which an oxygen-containing component contained in the organometallic compound can be removed from it and which is industrially advantageous. This and other objects of the present invention will become clear from the description hereinafter.

Extensive studies have been made in order to obtain an organometallic compound having a low oxygen content by an efficient purifying method thereof which is readily carried out industrially, and it has been found that the oxygen-containing component contained in the crude organometallic compound can be very efficiently removed in a simple way by treating the crude organometallic compound with an alkali halide to obtain a purified organometallic compound.

Accordingly, the present invention provides a process for removing an oxygen-containing component in a crude organometallic compound consisting essentially of an organometallic compound of the general formula (1):

$$R_1R_2MX \qquad (1)$$

wherein $R_1$ and $R_2$ independently represent an alkyl group or a cycloalkadienyl group, M represents a Ga atom or an In atom and X represents an alkyl group, a halogen atom or a hydrogen atom, and the oxygen-containing component as an impurity, which comprises the steps of mixing the crude organometallic compound and an alkali halide in an amount of 0.1 to 10% by weight of the crude organometallic compound, heat-treating the mixture, and vaporizing the organometallic compound for separation, the steps being carried out in a substantially oxygen-free atmosphere.

DETAILED DESCRIPTION OF THE INVENTION

The crude organometallic compound to be purified in the present invention consists essentially of the organometallic compound of the general formula (1) and the oxygen-containing component as an impurity.

The organometallic compounds of the general formula (1) include a trialkyl compound, a cycloalkadienyl dialkyl compound, a dicycloalkadienyl alkyl compound, a dialkyl halide compound or a dialkyl hydride compound of gallium or indium, in which the alkyl group usually contains 1 to 8, preferably 1 to 4 carbon atoms and the cycloalkadienyl group contains 5 to 8 carbon atoms. Examples of the organometallic compound of the general formula (1) are trimethyl gallium, triethyl gallium, tripropyl gallium, tributyl gallium, trineopentyl gallium, cyclopentadienyl dimethyl gallium, cyclopentadienyl diethyl gallium, methyl diethyl gallium, ethyl dimethyl gallium, trimethyl indium, triethyl indium, methyl diethyl indium, ethyl dimethyl indium, cyclopentadienyl dimethyl indium, cyclopentadienyl diethyl indium, dimethyl gallium chloride, diethyl gallium chloride, dimethyl indium chloride or diethyl indium chloride, etc. The oxygen-containing component may be an oxygen-containing compound or a mixture of at least two kinds of the oxygen-containing compound.

The oxygen-containing compound may be an alkoxy dialkyl compound, a cyclodienyl alkoxy alkyl compound, a dicyclodienyl alkoxy compound, an alkoxy alkyl halide compound, a hydroxy dialkyl compound, an alkoxy alkyl hydride compound, etc. of gallium or indium.

The alkali halides to be used include fluoride, chloride, bromide or iodide of lithium, sodium or potassium. The fluoride and chloride are preferred and the fluoride is more preferred.

An alkali halide is supposed to react with the oxygen-containing component to form a coordination compound. It is preferred to select an alkali halide which gives a coordination compound having a lower melting point in views of processability. For example, when trimethyl gallium or trimethyl indium is treated, KF is most preferred.

The alkali halide may be used alone or in admixture. It is desirably subjected to treatments such as dehydration by heating it under vacuum prior to its use. Size reduction thereof is also effective to increase its reactivity.

The equipment used in the present invention is required to prevent oxygen or moisture to be entered into the reaction system from the outside. The inert gas used is preferably purified to an oxygen content below about 0.5 ppm, for example, by a purifying instrument. Examples of the inert gas are argon, nitrogen, helium, etc. When a solvent is used, it is preferably gas-exchanged by bubbling an inert gas before it is used. The solvent is also preferred to be previously treated with a dehydrating agent if necessary. A substantially oxygen-free atmosphere can be thus achieved using such the apparatus, the inert gas and the solvent.

The crude organometallic compound is mixed with an alkali halide, and then the mixture is heat-treated. The mixing and heat treatment may also be carried out concurrently. The heat treatment is carried out usually at a temperature of not lower than 50° C., preferably not lower than 60° C., more preferably under reflux, usually for 10 minutes to 3 hours.

The heat treatment can be effected optionally in the presence of a solvent. The solvents to be used include hydrocarbons such as hexane, heptane, octane, dodecane, cyclohexane, etc.

An amount of the alkali halide to be used is in the range of 0.1 to 10% by weight, preferably 1 to 5% by weight, based on the weight of the crude organometallic compound, although it depends on the amount of the oxygen-containing component contained in the crude organometallic compound.

In addition to the alkali halide, simultaneous addition of a small amount of an alkyl aluminum, particularly trimethyl aluminum, may provide further purifying effect in some cases. The alkyl aluminum is added usually in an amount of 0.5 to 5% by weight, based on the weight of the crude organometallic compound to be treated. In the case, in addition to the alkali halide in the amount as described above, the alkali halide is added preferably in an amount which is required and necessary for forming a coordination compound with the alkyl aluminum, for example, about 1.2 to 2 moles per mole of the alkyl aluminum. Since the alkyl aluminum forms a coordination compound with an alkali halide and/or the oxygen-containing component, it can be separated from a purified organometallic compound by means of distillation, sublimation or the like, like the oxygen containing component.

The heat-treated mixture is then subjected to distillation or sublimation treatment. Prior to distillation, a separating procedure such as filtration may be optionally carried out if necessary. Distillation or sublimation can be effected in a manner under a condition usually employed, which can be selected taking into consideration of properties and purity of the crude organometallic compound to be treated. The purified organometallic compound is obtained as a distillate or a sublimate while the coordination compound containing the oxygen-containing component remains as a residue.

In one embodiment of the present invention, the treatment may be carried out in a MOCVD cylinder. That is, an alkali halide is previously charged in the cylinder, then an crude organometallic compound is added in such an amount that the alkali halide is in the concentration range described above, and the mixture is heat-treated. Then a carrier gas is flowed through the cylinder, whereby the purified organometallic compound is entrainment-vaporized to be separated from the oxygen-containing component. In this embodiment, there is no need for the distillation or sublimation of the heat-treated mixture. In the case, the entrainment-vaporization of the organometallic compound by the flow of the carrier gas corresponds to the above mentioned distillation or sublimation treatment. In the present invention, the term "vaporizing the organometallic compound for separation" includes distillation, sublimation and the entrainment-vaporization treatment. As a carrier gas, which is used for the entrainment-vaporization of the organometallic compound by the flow thereof, hydrogen gas is usually used and the inert gas described above may also be used.

The entrainment-vaporizing treatment in the process according to the present invention can serve also as a vaporizing process of the organometallic compound in MOCVD. Therefore, contamination with oxygen caused during the charge of the organometallic compound into a MOCVD cylinder for a MOCVD can be also avoided.

In the present invention, a content of the oxygen-containing component is represented by content of oxygen therein.

Total content of the oxygen-containing component in the purified organometallic compound obtained by the present invention is usually not more than 100 ppm, preferably not more than 50 ppm, more preferably not more than 30 ppm.

According to the present invention described in detail above, the oxygen-containing component generated by the oxygen or the moisture inevitably mixed during procedures for preparing or dealing the organometallic compound can be removed from the organometallic compound in a simple way by treating it with the alkali halide to obtain an organometallic compound in high quality. Therefore it can be advantageously used in the field of electronic materials.

EXAMPLES

The present invention will be illustrated in more detail hereinafter.

The oxygen-containing component in the organometallic compound were analyzed in the following way: An amount of water deoxygenated by nitrogen bubbling and dodecane as a solvent are previously charged in a sealed stainless steel vessel. After cooling the system, it is evacuated. The organometallic compound, which is a sample, is then introduced through a metering tube having a specific capacity into the system and the reaction mixture is allowed to be left in the sealed condition to a room temperature to hydrolyze it for a sufficient period. Then the content is taken out and the alcohol content contained in a water layer is analyzed by gas chromatography. After it is converted to the weight of an oxygen atom, an oxygen component concentration in the sample is shown as a weight concentration of oxygen in the sample.

An analysis of aluminum was effected by inductivity coupled plasma emission spectroscopy method (ICP method).

Example 1

A 200 ml flask equipped with a stirrer and a reflux condenser was filled with nitrogen after it had been evacuated. Then, 100 g of crude trimethyl gallium was charged therein, followed by gradual charging of 3 g of dried potassium fluoride, and the mixture was gradually heated and maintained at 56° C. for 1 hour under reflux.

Then the mixture was distilled at 56° C. under a normal pressure to obtain 84.5 g of purified trimethyl gallium. Analyses showed an oxygen component concentration of 85 ppm in the crude trimethyl gallium and 5 ppm in the purified trimethyl gallium.

Example 2

A 200 ml flask equipped with a stirrer and a reflux condenser was filled with nitrogen after it had been evacuated. Then, 50 g of crude trimethyl indium and 0.6 g of dried potassium fluoride were charged therein, and the mixture was gradually heated and stirred at 100° C. for 1 hour.

Then the mixture was distilled at 130° C. under a reduced pressure of 275 Torr to obtain 42 g of purified trimethyl indium. Analyses showed an oxygen component concentration of 220 ppm in the crude trimethyl indium and 12 ppm in the purified trimethyl indium.

Example 3

Example 2 was repeated except that 0.3 g of trimethyl aluminum was mixed in addition to the crude trimethyl indium and potassium fluoride. 40.5 g of purified trimethyl indium, which had an oxygen component concentration of 7 ppm and an aluminum concentration of 20 ppm, was obtained.

Example 4

Into a 250 ml MOCVD cylinder, 145 g of alumina spheres having a diameter of 4 mm and 1 g of dried potassium fluoride were charged and the system was filled with argon after it had been evacuated. 52 g of crude trimethyl indium was added thereto and a valve was closed. The cylinder was then allowed to rotate in a sealed state at 100° C. for 1 hour. Then an hydrogen gas was flowed at 20° C. at a rate of 400 ml/min. through the cylinder and 47 g of purified trimethyl indium entrained with the hydrogen gas was collected at a dried ice temperature. Analyses showed that the values of concentration of the oxygen component were 350 ppm in the crude trimethyl indium and 30 ppm in the purified trimethyl indium and the concentration of aluminum were 9 ppm in the crude trimethyl indium and 2 ppm in the purified trimethyl indium.

What is claimed is:

1. A process for removing an oxygen-containing component in a crude organometallic compound consisting essentially of an organometallic compound of the general formula (1):

$$R_1R_2MX \quad (1)$$

wherein $R_1$ and $R_2$ independently represent an alkyl group or a cycloalkadienyl group, M represents a Ga atom or an In atom and X represents an alkyl group, a halogen atom or a hydrogen atom, and the oxygen-containing component as an impurity, which comprises the steps of mixing the crude organometallic compound and an alkali halide in an amount of 0.1 to 10% by weight of the crude organometallic compound, heat-treating the mixture, and vaporizing the organometallic compound for separation, the steps being carried out in a substantially oxygen-free atmosphere.

2. A process as claimed in claim 1, in which the alkali halide is a compound selected from the group consisting of fluoride, chloride, bromide and iodide of Li, Na and K.

3. A process as claimed in claim 1, in which the alkali halide is potassium fluoride.

4. A process as claimed in claim 1, in which the organometallic compound is a compound selected from the group consisting of a trialkyl compound, a cycloalkadienyl dialkyl compound, a dicycloalkadienyl alkyl compound, a dialkyl halide compound and a dialkyl hydride compound of Ga and In.

5. A process as claimed in claim 4, in which the organometallic compound is a compound selected from the group consisting of trimethyl gallium, triethyl gallium, tripropyl gallium, tributyl gallium, trineopentyl gallium, cyclopentadienyl dimethyl gallium, cyclopentadienyl diethyl gallium, methyl diethyl gallium, ethyl dimethyl gallium, trimethyl indium, triethyl indium, methyl diethyl indium, ethyl dimethyl indium, cyclopentadienyl dimethyl indium, cyclopentadienyl diethyl indium, dimethyl gallium chloride, diethyl gallium chloride, dimethyl indium chloride and diethyl indium chloride.

6. A process as claimed in claim 3, in which the organometallic compound is trimethyl indium.

7. A process as claimed in claim 1, in which an alkyl aluminum is further mixed in an amount of 0.5 to 5% by weight of the crude organometallic compound in addition to the crude organometallic compound and the alkali halide in the step of mixing.

8. A process as claimed in claim 1, in which the vaporization is an entrainment-vaporization by a flow of an inert gas or hydrogen gas.

9. A process as claimed in claim 8, in which the entrainment-vaporization is carried out by a flow of a hydrogen gas.

10. A process as claimed in claim 1, in which the vaporization is carried out by distillation or sublimation.

* * * * *